United States Patent [19]

Berkman et al.

[11] 4,022,256
[45] May 10, 1977

[54] ASEPTIC FLUID TRANSFER SYSTEM

[75] Inventors: Richard M. Berkman, Pasadena;
James C. Arnett, La Canada;
Edward L. Cleland, Duarte, all of Calif.

[73] Assignee: California Institute of Technology, Pasadena, Calif.

[22] Filed: Sept. 25, 1975

[21] Appl. No.: 616,765

Related U.S. Application Data

[63] Continuation-in-part of Ser. No. 602,271, Aug. 6, 1975, abandoned.

[52] U.S. Cl. .................................... 141/1; 141/98; 156/289

[51] Int. Cl.² ............................................ B65B 3/04
[58] Field of Search .............. 141/1, 98; 156/250, 156/251, 252, 253, 261, 289, 306

[56] References Cited

UNITED STATES PATENTS 3,640,790  2/1972  Rowley et al. .................... 156/251

*Primary Examiner*—Houston S. Bell
*Attorney, Agent, or Firm*—Lindenberg, Freilich

[57] ABSTRACT

A method and means is provided, which permits the transfer of fluids between separate detached containers, in a manner which preserves the sterility of the fluids during and after their transfer.

26 Claims, 15 Drawing Figures

ASEPTIC FLUID TRANSFER SYSTEM

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

This application is a continuation-in-part of application Ser. No. 602,271, filed Aug. 6, 1975, now abandoned.

BACKGROUND OF THE INVENTION

This invention relates to a method and means for providing a sterile transfer of fluids between two containers.

The problem of the sterile transfer of fluids arises in a number of different areas, however the most immediate need seems to be in the area of blood handling. Since blood contains several major different components, each serving a unique function, the use of whole blood for transfusion has become unnecessary in many cases. Instead required components can be removed, allowing the balance of the blood to be employed elsewhere. Thus, blood component therapy has helped to ease the blood shortage somewhat, at a time of rapidly increasing demand.

The red blood cell fraction represents the most widely used component of blood. About 70% of all blood transfusions call for red blood cells. Freezing methods allow red cells to be stored for many months without loss of quality, however, none of the present methods for processing frozen-thawed blood can guarantee sterility. A long-standing FDA ruling places a 24-hour outdating limit on blood once it has been thawed. The present ruling has evolved from an earlier FDA policy, still in effect, which places the same limit on blood or any blood component, once its sterility can no longer be assured. For some blood fractionation applications, the 24-hour outdate problem can be sidestepped by employing blood collection bags with one or more attached satellite bags. To remove plasma aseptically from a collection bag, for example, a bag of blood with an empty satellite bag attached is centrifuged and the supernatant fluid (plasma) can then be expressed into the satellite bag. The common tubing connecting the 2 bags is then sealed and detached, yielding a unit of "sterile" packed cells and the unit of "sterile" plasma.

Satellite bags supply however, only a partial answer to the sterility problem. The collection bags are cumbersome and costly. Furthermore, they solve neither the sterile entry problems associated with the cell washing, nor the sterility problems associated with frozen blood processing. Accordingly, there is still a need for a scheme for removal or addition of fluid which has assured sterility, without any of the prior art problems such as the satellite bag briefly described above.

OBJECTS AND SUMMARY OF THE INVENTION

An object of this invention is the provision of a method and means for enabling the aseptic transfer of a fluid or fluids between two separate detached containers.

Another object of the present invention is the provision of a new fluid transfer system wherein sterility is assured.

Another object of this invention is the provision of a simple and relatively inexpensive arrangement for the sterile transfer of fluids between two independent containers.

The foregoing and other objects of the invention are achieved in an arrangement wherein two sterile containers, one of which has a fluid which it is desired to transfer to the other, are each formed with a plastic tube, or have a tube coupled thereto as an extension from the interior of the respective containers. Each tube has near a closed end or somewhere along its length, a "sterile transfer region" comprising a plastic material ("Material One") which can be made to melt and flow at a sterilizing temperature. These sterile transfer regions which can have any desired closed cross sectional area, also contain a liner or window of a second material ("Material Two") on the inside which will not melt at the temperature at which ("Material One") melts and flows.

The containers are placed so that their sterile transfer regions, overlap and are pressed against one another in a manner so that where they are in contact there is a region of the meltable material, ("Material One") while the inside liners, ("Material Two") internally cover the walls opposite the location where the walls of the two sterile transfer regions touch. The region where the two sterile transfer regions touch is clamped together between the two opposing jaws of a heating device wherein one jaw may be flat surfaced.

A raised ridge is provided, which crosses the region of the pressed together necks. The raised ridge may be within one of the necks or alternatively the second opposing jaw may be provided with raised ridges with these ridges crossing over the region of the pressed together necks. Pressure is applied and the jaws are electrically heated through either a programmed or manually-determined temperature-time cycle, and are then cooled. The temperature of the jaws is sufficient to cause the meltable material to become a fluid which flows out from under the pressurized jaws. The unmeltable material however does not flow. The raised ridges direct the flow of the meltable material away from the raised, or ridge, areas. As a result, at the region at which the two sterile transfer regions are touching, the walls become fused into a common wall and there is an opening produced in this wall between the extensions of the two containers. The non-meltable "Material Two" maintains the system closed and sterile by bridging any openings in surfaces of the walls opposite the walls which are pressed in contact with one another, where any plastic material might have flowed away as a result of the heat and pressure which has been applied.

A fluid transfer can then occur from one container to the other and the sterility of the transfer is preserved and assured, since the operation was carried out at a sterilizing temperature and it was not necessary to open either of the tubes to the atmosphere during the perforating process. Furthermore, the fusing and formation of the common wall entrains and immobilizes any bacteria that might otherwise enter into the openings caused in the two tubes. After the fluid transfer, the sterile transfer region may be sealed off at locations on either side, closer to each container and the two containers may then be separated by cutting them apart at the region between the sealed locations.

DESCRIPTION OF THE PREFERRED EMBODIMENTS

Figure 1:
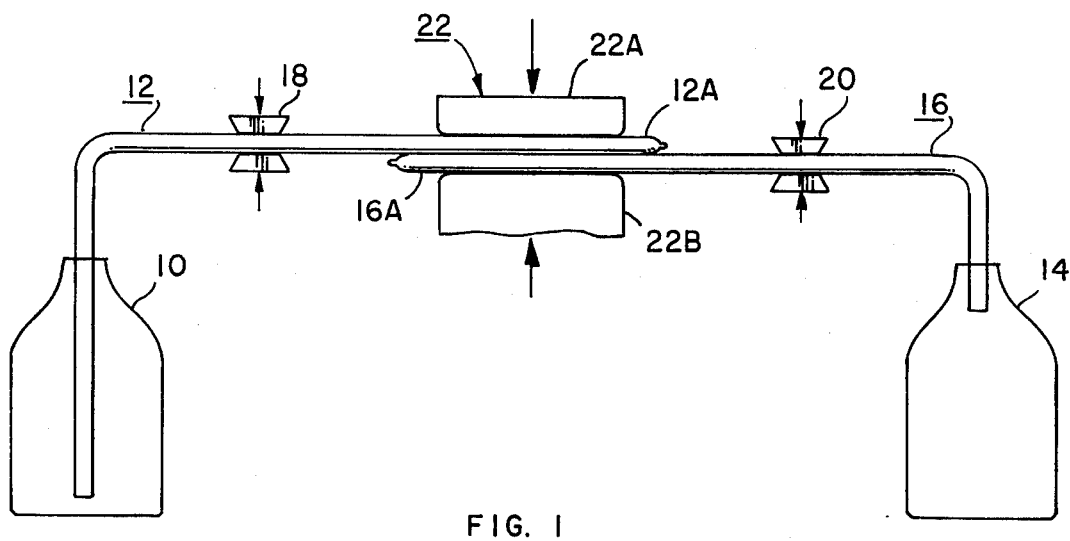
FIG. 1 is a schematic diagram illustrating placement of extensions from two bottles for the purpose of carrying a sterile transfer of fluids between the bottles, in accordance with this invention.

FIG. 1 is a schematic diagram of one embodiment of an aseptic fluid transfer system in accordance with this invention. A conventional sterile container 10, of fluids such as blood, is fitted with a flexible sterile plastic tube 12, which extends out of its neck as shown. Another sterile container 14, is similarly fitted with a neck extension 16. These tubular extensions 12, 16, are sealed at their ends as shown (12A and 16A). They may be made integral with the containers or made separately for later attachment to containers.

If required, clamps respectively 18, 20, may be used to hold predetermined regions of the sealed ends of the tubes 12, 16 in an overlapping relation, between the jaws respectively 22A, 22B, of a clamp 22. This latter clamp is heated to a heat sterilizing temperature and serves, first, to heat sterilize the external surfaces of the tubing where a specific fluid transfer is to occur, and second, to form a sterile passageway between the two tubes so that the sterile fluid can pass from the container 10 to the container 14, and back to container 10 if desired.

Figures 2, 3:
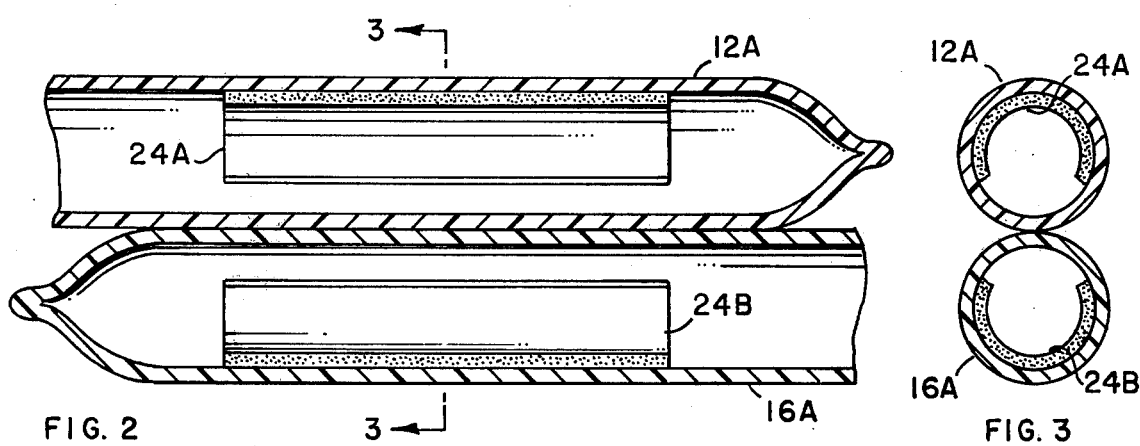
FIG. 2 is a cross-sectional view of the extensions from the two bottles showing their appearance at the overlapping region.
FIG. 3 is a cross-sectional view along the lines 3—3 of FIG. 2.

FIGS. 2 and 3 show an enlarged view in cross-section of the regions of the tubing which are made to overlap one another between the jaws of the clamp 22. These regions 12A and 16A, are sealed at one end as shown, and have a similar construction. Each tube including the region is fabricated from a material such as polyvinyl chlolride (PVC) or fluorinated ethylene propylene copolymer (Teflon-FEP), or other plastic materials, which will melt and flow and can be heat sealed at or above the sterilizing temperatures. Any temperature equal to or above the melting point is a sterilizng temperature. The Teflon-FEP material requires a temperature on the order of 290° C. PVC requires a temperature on the order of 185° C. Other suitable materials are surface activated species of Teflon-FEP, chlorotrifluoro-ethylene polymers (Kel-f), polyvinylidene chloride polymers (Saran).

Figure 4:
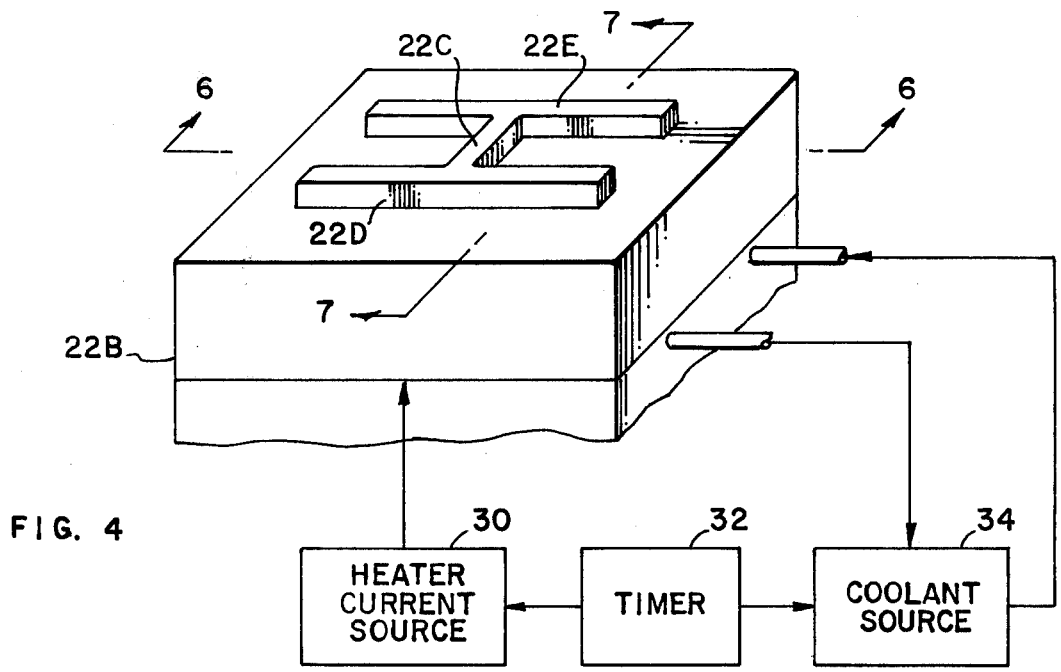
FIG. 4 is a schematic isometric view of the lower jaw of the clamp used in accordance with this invention.

Attached to part of the inside walls of each of the overlapping regions of the terminals is a material respectively, 24A, 24B ("Material Two"), which does not melt and is not heat sealable at the temperature of the remainder of the heated tubing. This material may also be a plastic material. A preferred material is Kapton, a polyimide film material, manufactured and sold by E. I. duPont de Nemours & Co. (Inc.) of Delaware. One embodiment of the invention employs a composite laminate which consists of Kapton on one side and Teflon-FEP on the other side. Because the Teflon-FEP surface of the laminate is meltable and heat sealable at the temperatures discussed, it simplifies bonding of the Kapton to the inside surfaces of the Teflon-FEP constructed terminals, allowing the Kapton to be bonded without an adhesive. As seen in the drawing, the Kapton ("Material Two") or material which is hereafter referred to as the liner material, is attached to the wall of all internal surfaces where corresponding external surfaces directly contact the heated clamp jaws. Surfaces in contact with the heated jaws are directly opposed to those surfaces where melting, fusing and penetration occur. The upper jaw of the clamp is simply a flat plate. FIG. 4 is a perspective view of one embodiment of the lower jaw of the clamp. This comprises, by way of example, a raised H on a flat plate wherein the crossbar 22C of the H effectively is at right angles to the terminals when they are placed within the clamp. The shape of the ridge on the lower jaw is illustrative, and should not be construed as a limitation upon the invention. What is required of the lower jaw, which will become more clear as this explanation progresses, is a configuration wherein the meltable material of the terminal is melted across the clamped regions of the terminal thereby permitting a sealed opening to be made through the adjacent walls of the clamped connectors in the region of the liner material. Thus the H-shaped ridges only on one jaw should be considered as illustrative only.

The jaws of the clamp are supplied with a heater current from the heater current source 30 under control of the timer 32. After the heater current is on long enough to enable Material One to melt and flow, the timer turns off the heater current and turns on a flow of coolant from a coolant source 34, to cool the jaws of the clamp. The use of a coolant is for the purpose of speeding up the operation. If desired, the jaws may be allowed to cool down to a temperature at which Material One solidifies without the use of a coolant. The cross bar of the lower jaw of the clamp may hereafter be referred to as the penetrator, 22C.

If desired, or required in order to insure sterility, the terminal material may be heated up to a sterilizing temperature and maintained at that temperature long enough to insure sterility. The temperature may then be increased further to the melting temperature. It is intended to include both the single as well as the two step heating process within the scope of this invention.

Figure 5:
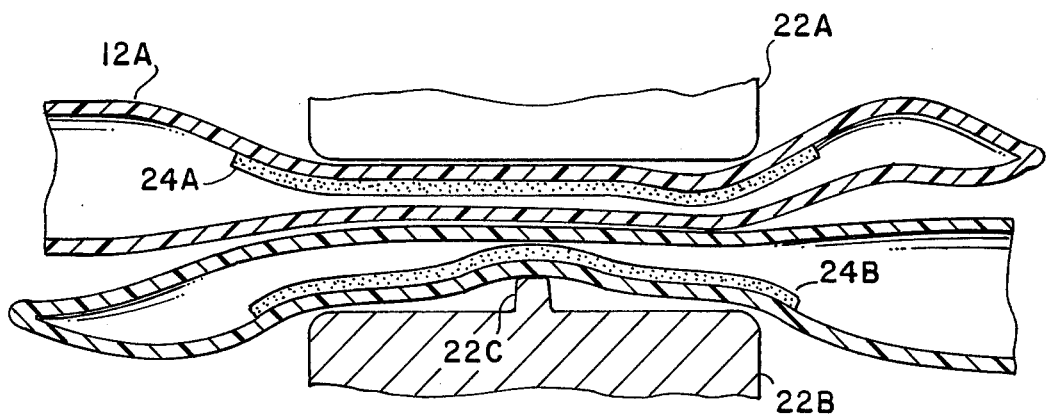
FIG. 5 is a cross-sectional enlarged view illustrating what happens when the two jaws clamp the extensions of the two vessels together.

FIG. 5 is a view in cross-section illustrating the deformation which the tubing regions undergo between the jaws of the clamp prior to the application of heat. (In a flat tube configuration, the tubes are compressed and need not deform).

Figure 6:
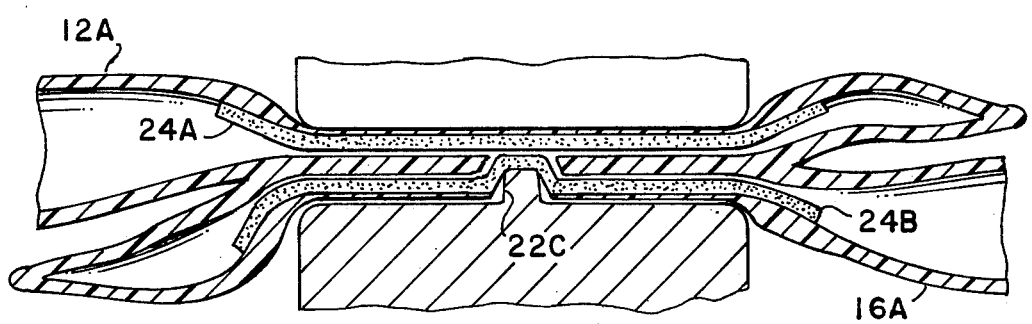
FIG. 6 is a view along the lines 6—6 of FIG. 4 illustrating what happens to the extensions as a result of the application of heat.

FIG. 6 is a cross-sectional view of the same region illustrating what happens upon the application of heat which raises the temperature of the material of the terminals (except for the lining material 24A, 24B), to their melting and flowing temperatures. It will be seen in FIG. 5 that the two separate connectors preserve their separate identities under the application of pressure. However, upon the application of heat, as well as pressure, the plastic Teflon-FEP material of the connectors flows away from the pressure area which in FIG. 6 comprises the penetrator 22C, whereby the lining materials 24A, 24B, effectively are pushed together, squeezing out the meltable material between them. This creates an opening between the two regions, 12A 16A at the pressure area, which is sterile, and still separated from the outside, in view of the presence of the non-melting liners 24A, 24B, which however remain intact and sealed to the regions of the tubing which are not caused to flow. It was pointed out that the liner material employed, preferably, Kapton, is actually a laminate with a Teflon-FEP coating on one side. This coating is one which is structurally heat sealable to the Teflon-FEP material of the tubular extension, or is attached by mechanical embedment in PVC or other thermoplastics with and without using adhesives.

While the embodiment of the invention shows liner material already sealed or attached to the material of the tubular extension, this should not be construed as a limitation upon the invention, since such sealing or attachment can occur either prior to the positioning of the terminals between the jaws of the clamp, or can be made to occur at the time the two terminals are compressed between the jaws of the clamp and have heat and pressure applied thereto. Thus the phrase, "attaching a liner material to the inside wall of each tubular extension," as used herein and in the claims, is intended to cover liner attachment prior to or during the sequence of the sterile transfer operation.

Figure 7:
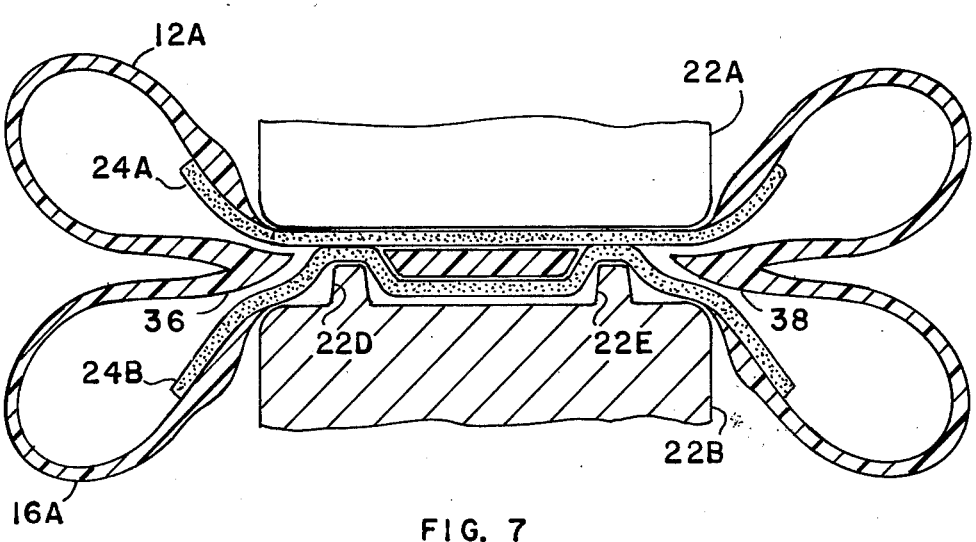
FIG. 7 is a view along the lines 7—7 of FIG. 4, illustrating, again, what happens as a result of the application of pressure and heat at this region.

FIG. 7 is a view, in section, along the line 7-7 of FIG. 4. It shows the appearance of the connectors after the application of heat and pressure. The pressure this time is provided by reason of the two sides respectively 22E, 22D of the ridged H on the lower jaw. It will be seen that here again the tubing material of the connectors flows away from the pressure points leaving only the lining material at these regions, which, however, is sealed to the tubing material, so that exposure to the outside is prevented and the sterility of the passageway created between the two transfer sections, as well as of the transfer regions themselves in the region between the jaws of the clamp is maintained. Further, the temperature to which the jaws of the clamp is raised is one which assures that sterility exists in those regions which may have been contaminated during handling before the heating sequence was initiated.

Figure 8:
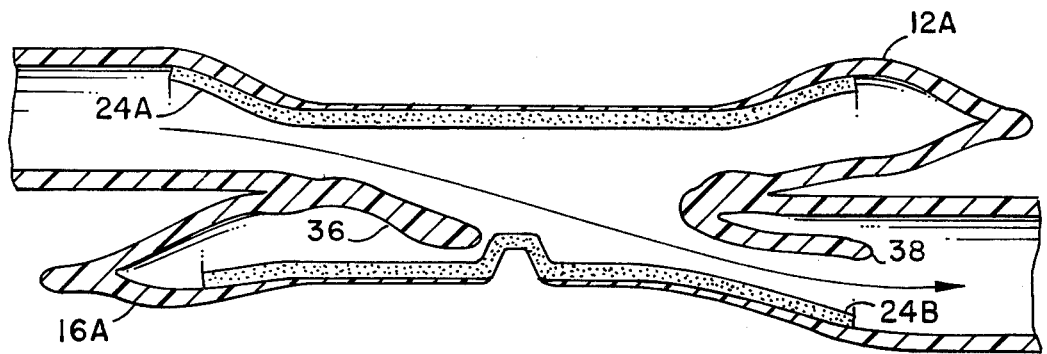
FIG. 8 is an enlarged cross-sectional view, illustrating the appearance of the junction of the neck extensions of the two vessels after they have been removed from the clamp.

FIG. 8 is a sectional view, similar to the sectional view of FIG. 5, only it is the appearance of the connector sections after they have been removed from the clamp. It will be seen that there is an open passage between the two terminal sections through which a fluid transfer can occur from the bottle containing the sterile fluid to a second sterile container. The liner material 24A, 24B adheres to the remaining wall section of the two regions preserving the sterility of the passageway therethrough. The melted material of the two adjacent walls of the connectors solidifies into one or more flaps, respectively 36, 38 in the connector sections. It will be noted that in FIG. 7, the walls of the connector sections 12A, 16A, are also sealed together into a common wall in the regions where they receive the heat and pressure from the jaws of the clamp.

While the foregoing description shows a single region of the tubing of two bottles being used for fluid transfer between two bottles, it should be apparent that by making the tubing long enough multiple sterile fluid transfers may be made from one bottle to others by starting with a transfer from near one end of the tubing from one bottle and then make succeeding transfers from successive regions of said tubing which are closer to the bottle. This is considered within the scope of the invention and the claims.

While the embodiment of the invention has been described referring to and showing cylindrical tubing, this should not be construed as a limitation upon the invention, since it will be apparent that cross-sectional areas, such as rectangular and other than cylindrical, may be used. Thus the word tubing as used herein and in the claims is intended to cover passageways having such other cross-sectional areas. Also, while the embodiment of the invention shows tubing extensions from the necks of the containers, this is not to be considered as a limitation upon the invention either. The neck or some other portion of the containers themselves may be used for providing a region where a sterile passageway may be made.

Figure 9:
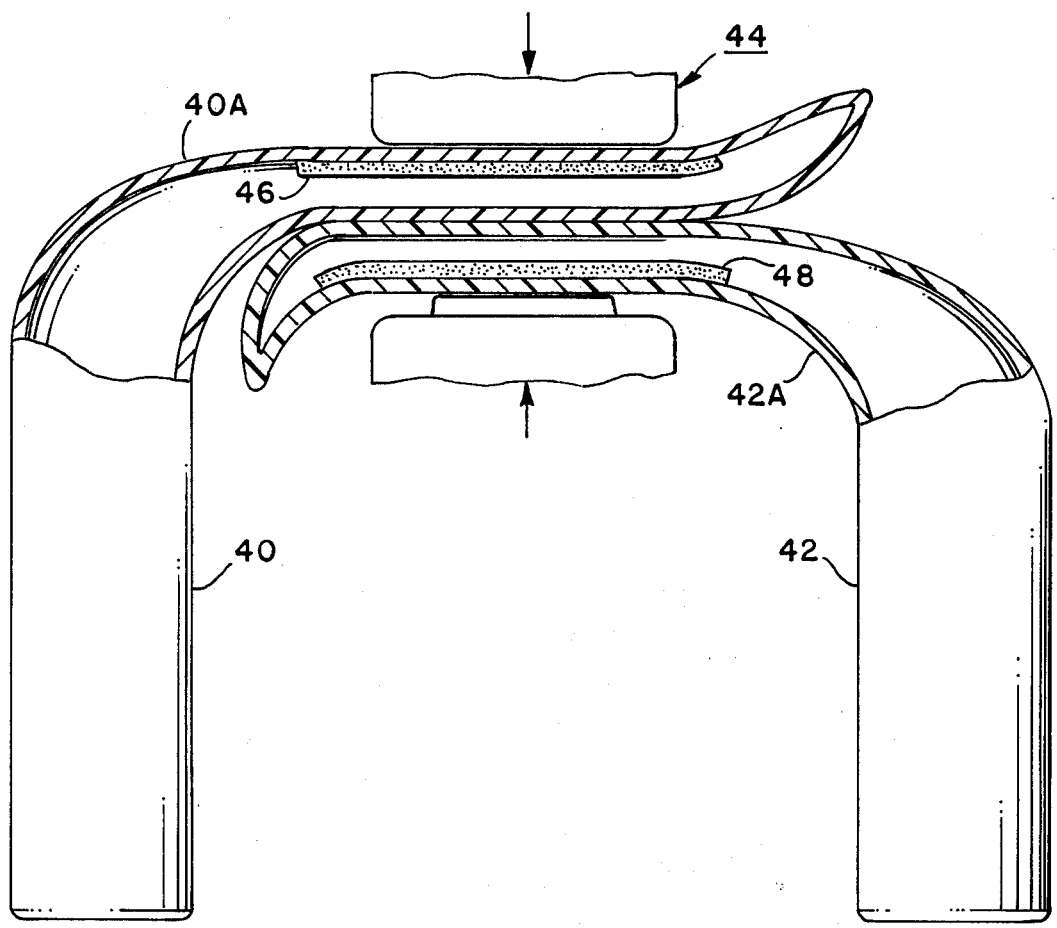
FIG. 9 illustrates how a sterile communicating opening can be obtained at a location within the two containers.

This is illustrated in FIG. 9 in cross section. Two sealed containers 40, 42, which may either be entirely made of PVC, Teflon-FEP or other heat sealable material or material combinations, or may be made of this material adjacent to and within the regions 40A, 42A, between the jaws of a clamp 44. Liner material 46, 48 is inserted inside the containers, in the regions between and adjacent to the jaws of the clamp covering as much of the inside walls as is required to insure that whatever size opening is made, is not so large as to open up the walls of the containers to the atmosphere.

The procedures and results achieved are, as has been previously described. After the sterile communicating passage and transfer of fluids has taken place, the containers can be heat sealed on either side of the region of the passageway, and the containers may then be separated by cutting through a region distant to the passageway, if such separation is desired.

Figure 10:
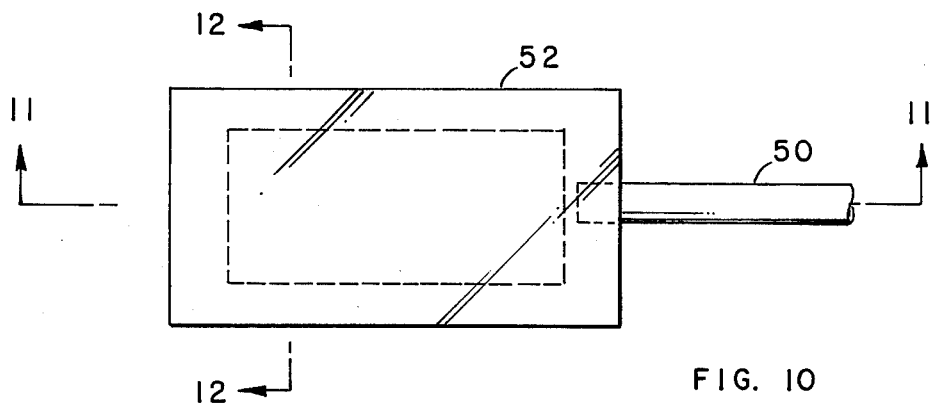
FIG. 10 is a plan view of a preferred arrangement for the region where a sterile passageway is established.
Figure 11:
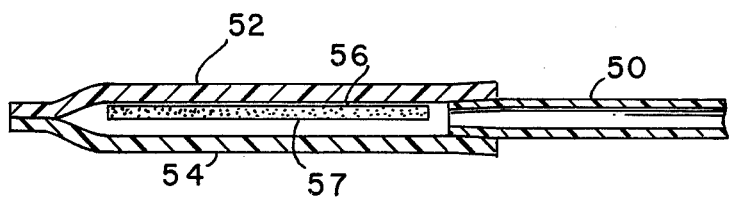
FIG. 11 is a cross-sectional view along the lines 11—11 of FIG. 10.
Figure 12:
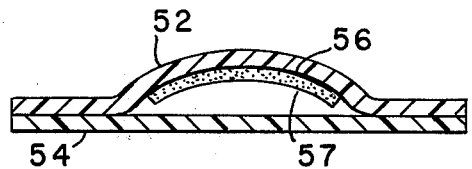
FIG. 12 is a cross-sectional view along the lines 12—12 of FIG. 10.

FIG. 10 illustrates a preferred arrangement of a sterile transfer region, in accordance with this invention. FIGS. 11 and 12 are respectively cross sectional views along the lines 11-11 and 12-12 of FIG. 10. This is a flat tube arrangement. PVC tubing 50, which extends from a bottle, is attached to two flat pieces of PVC, respectively 52, 54 which are glued or heat sealed at their edges to form a sealed envelope with entrance into the central opening of the envelope only being through the tubing 50. Prior to sealing, a piece of Kapton 56 is attached to the inside of one of the flat pieces 52 for the same purpose as was described in connection with the previous embodiments of the invention.

With this embodiment of the invention, it is preferred to use the Kapton-Teflon FEP laminate. However, since Teflon and PVC are not heat or pressure sealable to one another the Teflon FEP side 57 of the laminate is placed on the side away from the flat piece 52. The Teflon FEP layer now functions to prevent possible sticking to the opposite flat piece 54 when heat and pressure are applied to two flat tubes for the purpose of forming the sterile transfer openings.

FIG. 12 is an end view, in cross section, of the flat tube sterile transfer region and shows what happens after dry or wet sterilization of this region. The laminate curls and tends to change the shape of the central cavity to broaden it.

The reason this flat tube embodiment of the invention is preferred is because of the ease of manufacture. It will be understood that for the purpose of forming a sterile transfer passageway between two flat tubes they are placed one atop the other with the flat pieces of PVC bearing the Kapton-Teflon FEP laminates on the outsides, and then pressure and heat are a applied in the manner described previously.

Figure 13:
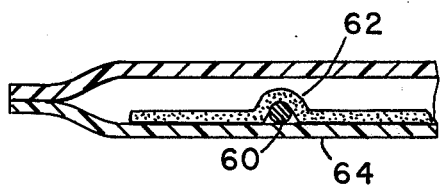
FIGS. 13 and 14 are cross-sectional views of the region where a sterile passageway is created illustrating an alternative placement of a ridge.
Figure 14:
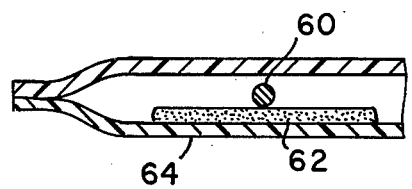

In the event that a clamp with ridges on one of the jaws is not available, FIGS. 13 and 14 illustrate, in cross section, an embodiment of the invention with which a clamp having two flat jaws may be used. An internal ridge may be provided. That is a hard cylindrical or rectangular bar 60, on the order of 2mm in diameter, or on a side, may be placed between the Kapton laminate 62 and the wall 64 of the region at which the sterile transfer opening is to be created. Alternatively as shown in FIG. 14 the rod 60 may be attached to the outside surface of the Kapton laminate. The rod extends across the length of the Kapton laminate. It may be made of metal or even Kapton or any other material which will not melt and which is sufficiently hard to cause the "Material One" walls of the sterile transfer regions to flow on either side thereof under the influence of heat and pressure.

Figure 15:
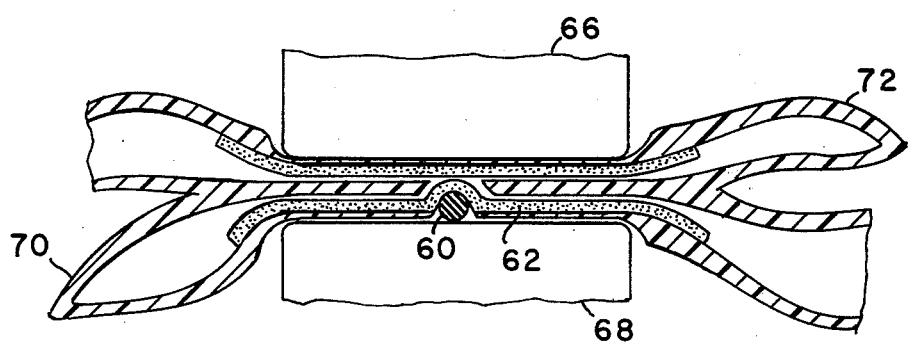
FIG. 15 is a cross sectional view illustrating how an internal ridge can establish a sterile passageway.

As may be seen in FIG. 15, only one of the rods is necessary for obtaining the necessary penetrations, just as a clamp requires ridges only on one jaw. In FIG. 15, the clamp has opposing jaws 66, 68 with flat faces. Under the influence of heat and pressure, the rod 60 will cause a penetration through the Material One walls, substantially similar to that which occurs when a clamp with one jaw with ridges is used. This penetration is shown in FIG. 15, and also shown are the flaps respectively 70, 72 which are formed on either side of the rod as a result of the wall material melting and flowing together on either side of the rod.

From the foregoing description, it should be apparent that there is provided an arrangement for making a connecting passageway, which is sterile, between two separate detached sterile containers, or between tubings emanating from separate detached sterile containers. These tubings can be made as part of the containers or may be separately manufactured with provision for attaching them to the containers in any well known manner, such as heat welding or gluing. After a transfer of fluid between the two containers has occurred, the two containers are sealed by applying a melting temperature to the walls of the individual containers or the tubing extending from each separate container, which is on one or both sides of the section where the common passageway has been established Once the tubing has been closed, then the passageway sections may be cut through.

It should be noted that because of the manner in which an opening is formed, in accordance with this invention, at the regions of perforation of adjacent walls to enable fluid transfer, the interiors of the passageways are never exposed and the only possible contamination can occur from the outsides of the perforated adjacent walls themselves. However, at the time the opening is made the perforated wall portions are formed into flaps thereby entraining and immobilizing any bacteria that might otherwise enter the passageway that has been created. Thus while the use of a sterilzing temperature is preferred at the time the passageway is created, this may not be necessary.

There has accordingly been shown and described a novel, useful, and simple, method and means for providing a sterile passageway between two separate detached sterile containers.

The embodiments of the invention in which an exclusive property or privilege is claimed is defined as follows:

1. A method for enabling an aseptic transfer of a fluid which is in one sterile container to another sterile container, comprising forming a connector portion of both containers out of a material which will melt and flow at a predetermined temperature, placing two predetermined lengths of said two portions in contact with one another, applying heat and pressure at said melting and flowing temperature, to predetermined areas of said connector portions within the lengths which are in contact to cause the material of said connector portions to flow away from said area to the regions around said area, to form a communicating opening over said areas between said contacting portions while maintaining sterile and closed all other regions of said portions, and cooling the areas of said connector portions whereby a sterile passageway is created through said portions for transferring fluid from one container to another.

2. The method as recited in claim 1 wherein said step of applying heat, while maintaining sterile and closed all other regions of said connector portions includes, attaching a separate liner to the inside walls of each of said connector portions which extends over said predetermined lengths and covers part of the inside walls, said liners being made of a material which does not melt and flow at said melting and flowing temperature, and the step of placing said two predetermined lengths of said two connector portions in pressng contact with one another includes placing over one another the said lengths of said connector portions with the portions of the walls to which said liners are not attached being pressed against one another.

3. A method for enabling an aseptic transfer of a fluid which is in one sterile container to another sterile container comprising making a sterile and sealed at one end tubular extension for each container out of a material which will melt and flow at a sterilizing temperature, attaching a liner, made of a material which does not melt and flow at the sterilizing temperature, to the inside wall of each tubular extension, opposite the site at which a fluid transfer is desired, which liner extends for a predetermined distance along the length of each of said extensions and covers part of the internal circumference thereof, placing over one another the regions of said tubular extensions having said liners with the portions of the walls of said two tubular extensions opposite said liners being pressed against one another, applying heat at said temperature which causes said tubular extension material to melt and sufficient pressure across a part of the pressed together regions of said tubular extensions to cause said material of said tubular extensions to flow away from the location at which pressure is applied and to join on both sides thereof maintaining the junction of said tubular extensions sterile and exposing said liners to each other whereby a sterile passageway is provided between said two containers, and cooling said tubular extension material, and withdrawing said pressure and clamping.

4. A method as recited in claim 3 where the material of said tubular extensions is one selected from the group consisting of fluorinated ethylene propylene polymers and surface activated species thereof, polyvinyl chloride polymers, chlorotrifluoro-ethylene polymers, and polyvinylidene chloride polymers, and the material of said liner is the polymide Kapton.

5. Apparatus for enabling the aseptic transfer of a fluid which is in one sterile container to another sterile container comprising a first and a second container, each container having a first and a second tubular portion made of material which will melt and flow at a sterilizing temperature, means for holding said tubular portions together with walls in contact with one another, means for applying pressure and said sterilizing temperature to predetermined areas within said held together tubular portions to cause the material of said tubular portions to melt and flow away from the areas of said predetermined pressure forming a communicating opening between said tubular portions, and insert means within said tubular portions for maintaining the walls of said tubular portions sealed except for said communicating opening, whereby upon cooling, a sterile sealed opening is provided between said tubular portions enabling an aseptic transfer of fluid therebetween.

6. Apparatus as recited in claim 5 wherein each said first and second tubular portions comprise a first and a second sheet of material having their ends joined to form a cavity therebetween, and means for connecting the respective cavities of the respective first and second tubular portions to the respective containers.

7. Apparatus as recited in claim 5 wherein said means for applying pressure and said sterilizing temperature comprises a rod adjacent to and extending across said insert means, said rod being made of a material which will not melt and flow at said first temperature and which is sufficiently hard at said first temperature to cause the material of said tubular portions to flow to either side thereof under the application of pressure at said first temperature, clamp means for applying pressure to said predetermined areas of said held together tubular portions, and means for applying heat to said clamp means to heat up said predetermined areas of said held together tubular portions to said sterilizing temperatures.

8. Apparatus as recited in claim 5 wherein said means for applying pressure and said sterilizing temperature comprises a clamp having one flat jaw, and an opposing jaw with raised ridges thereon, and means for applying heat at a sterilizing temperature to the jaws of said clamp.

9. Apparatus as recited in claim 5 wherein said insert means comprises a material which does not melt and run at said sterilizing temperature, and means for attaching said insert means to the walls of said tubular portion leaving exposed a portion of the walls which are in contact with one another and which include said predetermined areas.

10. Apparatus for enabling an aseptic transfer of a fluid which is in one sterile container to another sterile container comprising a first and a second container, each container having a connector portion made out of a material which will melt and flow at a sterilizing temperature, an insert for each connector portion attached to the inside wall, extending for a predetermined length thereof and covering part of the inside circumference of said inside wall, each said insert being made of a material that does not melt and flow at said sterilizing temperature, means for holding said connector portions together with those wall sections in contact wherein said liners are not present along the inside walls, means for applying pressure and said sterilizing temperature to predetermined regions within said held together connector portions to cause the material of said connector portions to melt and flow to either side of the predetermined regions enabling the inserts of said predetermined regions in each tubular portions to contact one another, and means for cooling said predetermined regions, whereupon a sterile sealed opening is provided between said connector portions enabling an aseptic transfer of fluids therebetween.

11. Apparatus as recited in claim 10, wherein each said connector portion comprises a first and a second sheet of material having their ends joined to form a cavity therebetween, and means for connecting the respective cavities of each said connector portion to the respective first and second containers.

12. Apparatus as recited in claim 10 wherein said means for applying pressure and said sterilizing temperature comprises a rod adjacent to and extending across said insert means, said rod being made of a material which will not melt and flow at said first temperature and which is sufficiently hard at said first temperature to cause the material of said tubular portions to flow to either side thereof under the application of pressure at said first temperature, clamp means for applying pressure to said predetermined areas of said held together tubular portions, and means for applying heat to said clamp means to heat up said predetermined areas of said held together tubular portions to said sterilizing temperatures.

13. Apparatus as recited in claim 10 wherein each said connector portion comprises a tube having one end in communication with a container and the other end sealed.

14. Apparatus as recited in claim 10 wherein said connector portions of said first and second containers comprise a material selected from a group consisting of fluorinated ethylene propylene polymers and surface activated species thereof polyvinyl chloride polymers, chlorotrifluoro-ethylene polymers, and polyvinylidene chloride polymers.

15. Apparatus as recited in claim 10 wherein said liner means comprises Kapton combined with Teflon-FEP.

16. A system for enabling the aseptic transfer of a fluid which is in one sterile container to another sterile container comprising, for each container,
   a sterile, sealed at one end, extension for the interior of a container made of a material which melts and flows at a sterilizing temperature,
   a liner for each extension, made of a material which does not melt at said sterilizing temperature, attached to the inside wall of each extension for a predetermined length thereof and covering part of said inside wall,
   clamping means for holding together with a first pressure said extensions at the regions having said liners but for a distance shorter than said liners, with the portions of the walls of said extensions opposite said liners being pressed against one another and for applying a second pressure higher than said first pressure across said tubular extensions to a limited area within the region which are held together,
   means for heating said clamping means to a temperature at which it causes said extension material to melt and flow to both sides of the limited area, and
   means for cooling said clamping means to permit said extension material to solidify, whereby an opening is provided between the two tubular extensions within said limited area of the application of second pressure with both said tubular extension walls being sealed to one another therearound.

17. A system, as recited in claim 16, wherein said clamping means has one jaw with a flat face and an opposing jaw to said one jaw with an "H" shaped raised portion positioned on a flat surface.

18. A system, as recited in claim 16 wherein said tubular extension material is one of the group consisting of flourinated ethylene propylene polymers and surface activated species thereof, polyvinyl chloride polymers, chlorotrifluorethylene polymers, and polyvinylidene chloride polymers.

19. A system as recited in claim 16 wherein said liner is made of polyimide (Kapton).

20. Apparatus for enabling the aseptic transfer of a fluid which is in one sterile container to another sterile container comprising for each container,
   connector means, having a central passageway, a closed end, and an open end for connecting said central passageway to a sterile container, said connector means being made of a material which melts and flows at a predetermined temperature, and
   an insert means adjacent an inside wall of said connector means, said insert means, being made of a material which remains solid at said predetermined temperature,
   said insert means having a length, shorter than the length of said central passageway and having a width such that it only covers part of the inside wall of said central passageway.

21. Apparatus as recited in claim 20 wherein a rod extends across and is adjacent to said insert means, said rod being made of a material which will not melt and flow at said first temperature, and which is sufficiently hard at said first temperature to cause the material of said connector means to flow to either side therof under the application of pressure at said first temperature.

22. Apparatus as recited in claim 21 wherein said rod is between said insert means and said inside wall.

23. Apparatus for enabling a transfer of a fluid from one container to another container comprising, for each container,
   a first and a second sheet of a material which melts and flows at a sterilizing temperature, said first and second sheets of material having their ends joined to form a cavity therebetween,
   a third sheet of a material which is smaller than either said first or second sheet and which does remain solid at said sterilizing temperature, and which is within said cavity and is positioned adjacent to said first sheet of material, and
   means for connecting said cavity to a container.

24. Apparatus as recited in claim 23 wherein said first and second sheets of material are made of polyvinyl chloride and said third sheet of material is made of Kapton.

25. Apparatus as recited in claim 23 wherein said first and second sheet of material are made of polyvinyl chloride and said third sheet of material is a laminate of Kapton and Teflon FEP, and wherein the Kapton side of said laminate is adjacent to said first sheet of material.

26. Apparatus as recited in claim 23 wherein a rod extends across and is adjacent to said insert means, said rod being made of a material which will not melt and flow at said first temperature, and which is sufficiently hard at said first temperature to cause the material of said first and second sheets to flow to either side thereof under the application of pressure at said first temperature.

* * * * *